(12) United States Patent
Faust et al.

(10) Patent No.: US 7,258,851 B2
(45) Date of Patent: Aug. 21, 2007

(54) CHOLESTEROL REDUCING CHEWING GUM COMPOSITION AND METHOD OF MAKING THE SAME

(75) Inventors: Steven Faust, Oak Ridge, NJ (US); Jesse J. Kiefer, Belvidere, NJ (US); Anthony John Bell, Andover, NJ (US)

(73) Assignee: Cadbury Adams USA LLC, Parsippany, NJ (US)

( * ) Notice: Subject to any disclaimer, the term of this patent is extended or adjusted under 35 U.S.C. 154(b) by 0 days.

(21) Appl. No.: 10/361,265

(22) Filed: Feb. 10, 2003

(65) Prior Publication Data

US 2004/0234459 A1 Nov. 25, 2004

Related U.S. Application Data

(63) Continuation-in-part of application No. 09/783,257, filed on Feb. 14, 2001, now abandoned.

(51) Int. Cl.
*A61K 9/68* (2006.01)
*A61K 9/00* (2006.01)

(52) U.S. Cl. .......................................... 424/48; 424/400

(58) Field of Classification Search ................ 424/439, 424/440, 48, 400
See application file for complete search history.

(56) References Cited

U.S. PATENT DOCUMENTS

| | | | |
|---|---|---|---|
| 4,980,178 A * | 12/1990 | Cherukuri et al. | |
| 5,156,866 A * | 10/1992 | Sato et al. | |
| 6,054,144 A * | 4/2000 | Burruano et al. | |
| 6,933,291 B2 * | 8/2005 | Qi et al. | |

* cited by examiner

*Primary Examiner*—Humera N Sheikh
(74) *Attorney, Agent, or Firm*—Hoffmann & Baron, LLP

(57) ABSTRACT

Center fill chewing gum compositions containing an effective amount of at least one stanol compound sufficient to provide a positive cholesterol effect in a warm-blooded animal including humans.

14 Claims, No Drawings

CHOLESTEROL REDUCING CHEWING GUM COMPOSITION AND METHOD OF MAKING THE SAME

RELATED APPLICATION

This is a Continuation-in-part Application of U.S. patent application Ser. No. 09/783,257, filed on Feb. 14, 2001 now abandoned.

FIELD OF THE INVENTION

The present invention is generally directed to a chewing gum composition which contains an amount of at least one plant stanol sufficient to obtain a positive cholesterol effect in humans. The present invention enables ingestion of an effective amount of the plant stanol without having to ingest large quantities of the chewing gum composition or having to ingest a relatively large number of individual servings of the chewing gum composition.

BACKGROUND OF THE INVENTION

Plant stanols and derivatives thereof (e.g., phytosterols and esters thereof) are known to possess health enhancing properties including imparting positive cholesterol effects such as reducing or lowering blood cholesterol levels. These compounds are generally referred to hereinafter as stanol compounds. Such naturally occurring products have a chemical structure similar to that of cholesterol. They are considered essential constituents for properly functioning cells. Stanol compounds are typically $C_{26}$-$C_{30}$ alcohols which have an aliphatic chain in the C-17 position. Stanol compounds are believed to reduce cholesterol by binding to cholesterol and thereby forming a complex, which is readily passed out of the body. Since high blood cholesterol levels have consistently been implicated as an important risk factor in cardiac and vascular diseases, the reduction of blood cholesterol is seen as a means of helping to prevent and/or reduce the effects of cardiac and vascular disease.

Stanol compounds have been combined with various food products to provide a convenient means of administering the active agent to humans. For example, there are currently two commercially available margarine based products known as Benecol (a trademark of Raisio Benecol Ltd, of Rasio Finland) and Take Control (a trademark of Lipton Company of Englewood Cliffs, N.J.), each of which contains a stanol compound. The stanol compound containing margarine is applied and used in a manner similar to conventional margarine products.

Other stanol compound-containing products are described, for example, in U.S. Pat. No. 5,591,836, which discloses the use of saponins bonded to sterols through a glycosidic linkage. The resulting complexes are used in a variety of products such as tablets, capsules, granules, cookies, wafers, candy products and the like for the purpose of reducing blood cholesterol levels.

WO99/15546 discloses the use of sistosterols as a dietary supplement in such food products as mustards, salad dressings, peanut butter, light spreads including margarine and mayonnaise as well as chocolate-flavored mint truffles.

WO98/58554 discloses the employment of a premix containing pulverized plant sterols and a conventional foodstuff raw material to prepare bakery products including bread, cake, pastries, crackers, biscuits, and the like.

European Patent Application No. 089767181 discloses the preparation of an aqueous dispersion of plant sterols and other high microlipids for use in spreads and other food products including beverages, dairy products, dry mixers, powdered non-dairy products, coffee, whiteners, milk shake mixes, confections, ice creams, instant milks, cake mixes, and the like.

Phytosterols have also been added to beverage compositions and acetic acid compositions such as disclosed in WO99/15547.

As indicated above, the incorporation of stanol compounds in wide variety of food products is known in the art. In many cases, the stanol compound is recognized as a cholesterol reducing agent. However, in order to obtain a cholesterol reducing effect in a human, the food product must be ingested in large quantities to provide a sufficient amount of the stanol compound to accomplish this purpose.

From a practical standpoint, the prior art food products contain r latively low levels of stanol compounds and therefore require the ingestion of large amounts of the food product to provide a sufficient amount of the stanol compounds in order to obtain a desired cholesterol reducing effect.

One particular class of food products incorporated with stanol compounds is chewing gum. The above problems encountered in the prior art are especially manifested in chewing gums. Stanol compounds especially plant stanols are oil soluble compounds, and they have a remarkably high affinity for the gum base employed in the making of chewing gum products. As a result, only a small portion of the stanol compound present in the chewing gum is released during chewing, while the rest of the stanol compound remains trapped in the gum base and unavailable to provide a positive cholesterol effect.

There are two major disadvantages of such chewing gums. First, the amount of the chewing gum, which must be chewed, is typically higher than the amount a consumer would consider convenient. Second, the chewing gum must be administered at least several times a day because individually the chewing gums are not able to deliver or do not contain sufficient stanol compounds to obtain a meaningful cholesterol reducing effect. Under these circumstances, the typical consumer is not likely to follow a regimen which requires ingestion of several and up to many individual servings of a chewing gum composition in order to obtain a cholesterol reducing effect. Such regimens have been problematical because they require discipline, and are contrary to acceptable chewing gum regimens for most humans.

To overcome this problem, it is theoretically possible to add higher amounts of stanol compounds per piece of chewing gum. However, high dosing of plant stanol compound adds significantly to the cost of producing such chewing gums, and may adversely affect the organoleptic and taste properties of the chewing gum.

A key to obtaining a positive cholesterol effect from chewing gums containing stanol compounds is to provide a chewing gum product which can deliver a desirable amount of the stanol compound in a small number of individual servings, preferably only one or two servings.

It would therefore be a significant advance in the art of reducing cholesterol if a chewing gum containing stanol compounds could be developed which contains a sufficient amount of stanol compounds that can be released at a suitable rate to furnish an effective positive cholesterol effect to aid in the overall nutritional regimen of the consumer.

It would be a further advance in the art if a chewing gum composition could be produced which can reduce cholesterol levels in a human in need of a reduction in cholesterol levels and can be readily adapted to a consumer's daily regimen over an extended period of time.

It would be a still further advance in the art if a chewing gum composition could be developed which is effective in providing a positive cholesterol effect but does not require the consumer to chew large volumes of a chewing gum product.

SUMMARY OF THE INVENTION

The present invention is generally directed to a composition in the form of a chewing gum composition, which provides an effective amount of at least one stanol compound during the course of a dosage regimen which is readily facilitated by the consumer.

In a further aspect of the present invention there is provided a chewing gum composition which delivers a positive cholesterol effect on humans by employing an effective amount of at least one stanol compound with a relatively small number of ingestable doses. In a preferred form of the present invention, the chewing gum composition of the present invention is formulated to enhance the release rate of the stanol compound contained therein and to provide a sufficient amount of the stanol compound such that a positive cholesterol effect is obtained through the ingestion of no more than seven doses of the chewing gum composition per day, preferably only one to four doses per day.

In a particular aspect of the present invention there is provided a stanol compound containing chewing gum composition comprising an outer shell enclosing at least one cavity and a liquid center within the at least one cavity, and the liquid center comprising an effective amount of at least one stanol compound sufficient in the course of a desirable dosage regimen to obtain a positive cholesterol effect. The outer shell comprises a gum base.

In a more particular aspect of the present invention there is provided a center fill chewing gum composition, which provides from about 1.0 to 2.0 grams of at least one stanol compound per day, preferably in no more than four to seven doses.

DETAILED DESCRIPTION OF THE INVENTION

The present invention is directed to a particular class of compositions containing stanol compounds which can be readily ingested by the consumer, employed in a relatively few doses and which is readily available. In particular, the stanol containing compositions of the present invention are in the form of chewing gum compositions which are formulated into chewing gum products for commercial retail sale to consumers whereby consumers are able to obtain a positive cholesterol effect by chewing a reasonable number of pieces of gum. The chewing gum composition of the present invention is formulated to enhance delivery and release of stanol compounds preferably in the form of plant stanols, which enables a positive cholesterol effect to be achieved with a reasonable number of individual chewing gum products. Further, by maintaining the content of stanol compounds at lower levels, the resulting chewing gum product exhibits good organoleptic and taste properties. The chewing gum of the present invention is especially suitable for use as part of a cholesterol reducing treatment regimen.

As used herein, a "positive cholesterol effect" shall be meant to be broad enough to include maintaining a relatively safe level of cholesterol in a human, and actually reducing the level of cholesterol in a human especially those having undesirably high levels of cholesterol.

Applicants have determined that by incorporating stanol compounds in center fill-type of chewing gum compositions the release rate and bioavailability of the stanol compounds is significantly enhanced over prior art chewing gum compositions. The center fill chewing gum compositions of the present invention can be formulated to effectively deliver to a consumer over the course of a typical day with an effective amount of stanol compound sufficient to impart a positive cholesterol effect to the consumer. As used herein the terms "center fill chewing gum" or "center fill chewing gum composition" shall mean any chewing gum composition or chewing gum product having an outer shell composed of a gum base enclosing at least one internal void or cavity, and a liquid center or center fill within the at least one cavity. It is understood that the center fill chewing gum composition of the present invention, instead of a single internal cavity, may be composed of multiple center fill containing cavities that are enclosed by the outer gum base shell thereof.

In particular, Applicants have discovered that by incorporating stanol compounds in center fill chewing gum compositions especially in the center fill or liquid center portion thereof, the rate at which the stanol compounds is released and delivered to the consumer is significantly enhanced, thereby improving delivery and bioavailability for obtaining a positive cholesterol effect. In this manner, the amount of stanol compounds normally required in prior art chewing gums may be effectively reduced.

As used herein the term "stanol compound" shall mean any stanol compound regardless of origin including plant stanols which is capable of providing a cholesterol reducing effect when administered to a consumer. The amount of the stanol compound, through the chewing of a relatively small number of doses of the chewing gum composition of the present invention, is sufficient to provide a sustainable positive cholesterol effect in the typical consumer. The stanol compound may be incorporated throughout the center fill chewing gum composition or only in a portion thereof preferably in the center fill portion thereof.

Stanol compounds as used herein include plant stanols, sterols and sterol fatty acid esters and derivatives thereof which have a cholesterol reducing effect. The stanol compounds for use in the present invention are essential components of all plants. They are similar in function to that of cholesterol in mammals. The most abundant stanol compounds are, for example, beta-sitosterol, campesterol, and stigmasterol. Other representative examples of stanol compounds include brassicasterol, cycloartenol, cyclobranol and the like.

Stanol compounds have been known to effectively reduce serum cholesterol levels when administered in sufficient quantities. Even when administered in relatively small doses (a few grams a day) they reduce the absorbability of cholesterol and thus lower the serum total and LDL-cholesterol levels. It appears that stanol compounds displace cholesterol from the micellar phase and thereby prevent its absorption. One of the problems mitigating against using stanol compounds to effectively reduce cholesterol levels is that the absorption rate of stanol compounds is typically less than five percent of the amount consumed.

In accordance with the present invention, there is provided a chewing gum composition preferably in the form of a center fill chewing gum which includes a sufficient amount of at least one stanol compound.

In a preferred embodiment of the present invention, there is provided a stanol compound containing chewing gum composition comprising an outer shell including gum base enclosing at least one cavity and a liquid center within the at least one cavity, and the liquid center including an amount of at least one stanol compound sufficient to be part of a regimen for providing an positive cholesterol effect. Preferably the effective amount of the stanol compound is from about 1 to 2 grams per day which is typically divided into a relatively small number of doses, up to seven doses per day. The effective amount is sufficient to achieve a positive cholesterol effect to the consumer. In general, the stanol compound is present in the liquid center in an amount from about 1% to 90%, and preferably from about 20% to 70% by weight based on the total weight of the chewing gum composition.

The present invention encompasses plant sterols, which are capable of delivering a positive cholesterol effect and maintaining the positive cholesterol effect when delivered in a chewing gum product in accordance with the present invention.

As previously indicated, stanol compounds include plant sterols which appear in the plant kingdom and which closely resemble the chemical structure of cholesterol. The sterols found in animals, plants and mushrooms of marine organisms and seaweeds form a wide variety of oxidation, double bond, methyl group substitution and C-17 side-group structures. Using a catalyst, phytosterols isolated in commercial applications can be hydrogenated into corresponding plant stanols. The most well known phytosterols are, for example, beta-sitosterol, stigmasterol, campesterol, brassicasterol, cycloartenol, and cyclobranol. The sources of stanol compounds in human diet include plant oils and margarines made from plant oils, while phytosterols can be found in grain products, soybeans and rice.

In accordance with the present invention, the stanol compounds which can be used in the products of the present invention are those which have a positive cholesterol effect (e.g., a cholesterol reducing effect) and which can be placed in relatively large quantities in such products without detracting from the organoleptic or taste properties of the chewing gum product.

In accordance with the present invention, the stanol compounds employed herein are combined with the ingredients of the products of the present invention in such an amount as to provide a positive cholesterol effect. The amount of the stanol compound, is preferably from about 100 to 500 mg per individual dose of the chewing gum product, preferably from about 300 mg to 480 mg per dose, to administer an effective amount of from about 1 to 2 grams of stanol compounds per day. The ingestion of one or two grams of stanol compounds results in a positive cholesterol effect which can be maintained when the dosage regimen is maintained by the consumer. Products for use in the present invention are those which can effectively include a meaningful dose of stanol compounds so that the consumer can chew a relatively few, preferably no more than four to seven portions of the product to achieve and maintain a positive cholesterol effect. In addition, the products are desirably easy to administer and easy to have at hand so that the consumer does not have to make special arrangements to take the desired amount of the stanol compound.

The ingredients used to formulate a center fill chewing gum composition are generally well known. The gum base formulation used to form the shell of the chewing gum composition generally includes gum base, elastomers, solvents, emulsifiers, plasticizers, fillers, sweeteners, flavors and the like.

Elastomers (rubbers) employed in the gum base of the present invention will vary depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, and the like, and mixtures thereof.

The amount of elastomer employed in the outer gum base portion will vary greatly depending upon various factors such as the type of gum base used, the consistency of the gum composition desired and the other components used in the composition to make the final chewing gum product. In general, the elastomer will be present in the gum base in an amount from about 0.5% to 20% by weight based on the total weight of the gum base, and preferably from about 2.5% to 15% by weight.

In addition to the components set out above, the gum base includes a variety of traditional ingredients, such as a component selected from the group consisting of elastomer solvents, emulsifiers, plasticizers, fillers, and mixtures thereof. These ingredients are present in the gum base in an amount to bring the total amount of gum base to 100% by weight based on the total weight of the gum base.

The gum base may contain elastomer solvents to aid in softening the elastomer component. Such elastomer solvents comprise, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to 15% by weight based on the total weight of the gum base, and preferably from about 7% to 11% by weight.

The gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. A preferred emulsifier is glyceryl monostearate. The emulsifier may be employed in amounts from about 2% to 15% by weight based on the total weight of the gum base, and preferably from about 7% to 11% by weight.

The gum base may also include plasticizers or softeners to provide a variety of desirable textures and consistency properties. Because of the low molecular weight of these ingredients, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to 20% by weight based on the total weight of the gum base, and preferably in amounts from about 9% to 17% by weight of the gum base.

Preferred plasticizers are the hydrogenated vegetable oils and include soybean oil and cottonseed oil which may be employed alone or in combination. These plasticizers provide the gum base with good texture and soft chew characteristics. These plasticizers and softeners are generally employed in amounts from about 5% to 14% by weight based on the total weight of the gum base, and preferably in amounts from about 5% to 13.5% by weight of the gum base.

In another preferred embodiment, the softening agent is anhydrous glycerin, such as the commercially available United States Pharmacopeia (USP) grade. Glycerin is a syrupy liquid with a sweet warm taste and has a sweetness of about 60% of that of cane sugar. Because glycerin is hygroscopic, it is important that the anhydrous glycerin be maintained under anhydrous conditions throughout the preparation of the chewing gum composition.

The gum base of this invention may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, and the like, and mixtures thereof. These fillers or adjuvants may be used in the gum base compositions in various amounts. Preferably the amount of filler, when used, will be present in an amount from about 15% to 40% by weight based on the total weight of the gum base, and preferably from about 20% to 30% by weight of the gum base.

A variety of traditional ingredients may be optionally included in the gum base in effective amounts such as coloring agents, antioxidants, preservatives, flavoring agents, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, and mixtures thereof, may also be included. Other conventional chewing gum additives known to one having ordinary skill in the chewing gum art may also be used in the gum base.

The present invention extends to methods of making the gum base. The manner in which the gum base components are admixed is not critical and is performed using standard techniques and apparatus known to those skilled in the art.

Once prepared, the gum base may be used directly as the outer shell of a center fill chewing gum, may be formulated with conventional additives to prepare a wide variety of chewing gum compositions for use as the outer shell of a center fill chewing gum, or may be stored for future use. The gum base may be used in sugar and sugarless containing chewing gum products to prepare a reduced-calorie containing gum product.

In another embodiment of the present invention, the gum base is formulated with additives such as a bulking agent, a sweetening agent, a flavoring agent, and the like, to form a chewing gum composition which is used as the outer shell of a center fill chewing gum. Additional sweetening agents, flavoring agents, and the like, may be included in the center fill portion or liquid center of the chewing gum composition. The amount of gum base employed in the chewing gum composition will vary depending on such factors as the type of gum base used, the consistency desired, and the other components used to make the final chewing gum product. In general, the gum base will be present in the chewing gum composition in an amount from about 40% to 85% by weight based on the total weight of the chewing gum composition, and preferably from about 50% to 65% by weight of the chewing gum composition.

The chewing gum composition of the present invention may include effective amounts of conventional additives selected from the group consisting of sweetening agents (sweeteners), plasticizers, softeners, emulsifiers, waxes, fillers, bulking agents (carriers, extenders), mineral adjuvants, flavoring agents (flavors, flavorings), coloring agents (colorants, colorings), antioxidants, acidulants, thickeners, and the like, and mixtures thereof. These ingredients are present in the chewing gum composition in an amount to bring the total amount of chewing gum composition to 100% by weight based on the total weight of the chewing gum composition. Some of these additives may serve more than one purpose. For example, in sugarless gum compositions, a sweetener, such as sorbitol or other sugar alcohol, may also function as a bulking agent.

The plasticizers, softening agents, mineral adjuvants, waxes and antioxidants discussed above, as being suitable for use in the gum base, may also be used in the chewing gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxymethyl cellulose, acidulants such as malic acid, adipic acid, citric acid, tartaric acid, fumaric acid, and mixtures thereof, and fillers, such as those discussed above under the category of mineral adjuvants.

The chewing gum composition of the present invention may also contain a bulking agent. Suitable bulking agents may be water-soluble and include sweetening agents selected from the group consisting of, but not limited to, monosaccharides, disaccharides, polysaccharides, sugar alcohols, and mixtures thereof; randomly bonded glucose polymers such as those polymers distributed under the tradename POLYDEXTROSE by Pfizer, Inc. of Groton in Connecticut; isomalt (a racemic mixture of alpha-D-glucopyranosyl-1,6-mannitol and alpha-D-glucopyranosyl-1,6-sorbitol manufactured under the tradename PALATINIT by Suddeutsche Zucker), maltodextrins; hydrogenated starch hydrolysates; hydrogenated hexoses; hydrogenated disaccharides; minerals, such as calcium carbonate, talc, titanium dioxide, dicalcium phosphate, celluloses and the and the like, and mixtures thereof. Bulking agents may be used in amounts up to 60% by weight based on the total weight of the chewing gum composition, and preferably in amounts from about 15% to 60% by weight of the chewing gum composition.

Suitable sugar bulking agents include monosaccharides, disaccharides and polysaccharides such as xylose, ribulose, glucose (dextrose), mannose, galactose, fructose (levulose), sucrose (sugar), maltose, invert sugar, partially hydrolyzed starch and corn syrup solids, and mixtures thereof. Mixtures of sucrose and corn syrup solids are the preferred sugar bulking agents.

Suitable sugar alcohol bulking agents include sorbitol, xylitol, mannitol, galactitol, maltitol, and mixtures thereof. Mixtures of sorbitol and mannitol are the preferred sugar alcohol bulking agents.

Maltitol is a sweet, water-soluble sugar alcohol useful as a bulking agent in the preparation of beverages and foodstuffs and is more fully described in U.S. Pat. No. 3,708,396, which disclosure is incorporated herein by reference. Maltitol is made by hydrogenation of maltose which is the most common reducing disaccharide and is found in starch and other natural products.

Suitable hydrogenated starch hydrolysates include those disclosed in U.S. Pat. Nos. 25,959, 3,356,811, 4,279,931 and various hydrogenated glucose syrups and/or powders which contain sorbitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN, a commercially available product manufactured by Roquette Freres of France, and HYSTAR, a commercially available product manufactured by Lonza, Inc. of Fairlawn in New Jersey, are also useful.

The sweetening agents used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Further preferred are high-intensity sweeteners including, for example, aspartame and neotame. Without being limited to particular sweeteners, representative categories and examples include:

(a) water-soluble sweetening agents such asdihydrochalcones, monellin, steviosides, glycyrrhizin, dihydroflavenol, and sugar alcohols such as sorbitol, mannitol, maltitol, and L-aminodicarboxylic acid aminoalkenoic acid ester amides, such as those disclosed in U.S. Pat. No. 4,619,834, which disclosure is incorporated herein by reference, and the like, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like, and mixtures thereof;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(l-cyclohexen)-alanine, N-[N-(3,3-dimethylbutyl)-L-alpha-aspartyl]-L-phenylalanine 1-methylester (Neotame), and the like, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructo-furanoside, or 4,1'-dichloro-4,1'-dideoxygalactosucrose; 1',6'-dichloro-1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro-4,6,1',6'-tetradeoxygalacto-sucrose; and 4,6,1',6'-tetradeoxy-sucrose, and the like, and mixtures thereof; and (e) protein based sweeteners such as thaumaoccous danielli (Thaumatin I and II) and the like, and mixtures thereof.

The intense sweetening agents of the present invention may be used in many distinct physical forms well known in the art to provide an initial burst of sweetness and/or a prolonged sensation of sweetness. Without being limited thereto, such physical forms include free forms, such as spray dried, powdered, and beaded forms, and encapsulated forms, and mixtures thereof.

In general, an effective amount of sweetener is utilized to provide the level of sweetness desired, and this amount will vary with the sweetener selected. The amount of sweetener will normally be present in amounts from about 0.001% to 3% by weight based on the total weight of the chewing gum composition, depending upon the sweetener used. The exact range of amounts for each type of sweetener is well known in the art and is not the subject of the present invention.

The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, mixtures thereof and the like.

The flavoring agent may be employed in either liquid form and/or dried form. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated. The actual techniques for preparing such dried forms are well known and do not constitute a part of this invention.

The flavoring agents of the present invention may be used in many distinct physical forms well known in the art to provide an initial burst of flavor and/or a prolonged sensation of flavor. Without being limited thereto, such physical forms include free forms, such as spray dried, powdered, and beaded forms, and encapsulated forms, and mixtures thereof.

The amount of flavoring agent employed herein is normally a matter of preference subject to such factors as the type of final chewing gum composition, the individual flavor, the gum base employed, and the strength of flavor desired. Thus, the amount of flavoring may be varied in order to obtain the result desired in the final product and such variations are within the capabilities of those skilled in the art without the need for undue experimentation. In chewing gum compositions, the flavoring agent is generally present in amounts from about 0.02% to 5% by weight based on the total weight of the chewing gum composition, and preferably from about 0.1% to 2% by weight of the chewing gum composition, and more preferably, from about 0.8% to 1.8% by weight of the chewing gum composition.

The coloring agents useful in the present invention are used in amounts effective to produce the desired color. These coloring agents include pigments, which may be incorporated in amounts up to about 6% by weight based on the total weight of the chewing gum composition. A preferred pigment, titanium dioxide, may be incorporated in amounts up to about 2% by weight based on the total weight of the chewing gum composition, and preferably less than about 1% by weight of the gum composition. The colorants may also include natural food colors and dyes suitable for food, drug and cosmetic applications. These colorants are known as F.D.&C. dyes and lakes. The materials acceptable for the foregoing uses are preferably water-soluble. Illustrative nonlimiting examples include the indigoid dye known as F.D.&C. Blue No.2, which is the disodium salt of 5,5-indigotindisulfonic acid. Similarly, the dye known as F.D.&C. Green No.1 comprises a triphenylmethane dye and is the monosodium salt of 4-[4-(N-ethyl-p-sulfoniumbenzylamino) diphenylmethylene]-[1-(N-ethyl —N-p-sulfoniumbenzyl)-delta-2,5-cyclohexadieneimine]. A full recitation of all F.D.&C. colorants and their corresponding chemical structures may be found in the Kirk-Othmer Encyclopedia of Chemical Technology, 3rd Edition, in volume 5 at pages 857-884, which the contents are incorporated herein by reference.

Suitable oils and fats usable in gum compositions include partially hydrogenated vegetable or animal fats, such as coconut oil, palm kernel oil, beef tallow, lard, and the like. These ingredients when used are generally present in amounts up to about 7% by weight based on the total weight of the chewing gum composition, and preferably up to about 3.5% by weight of the chewing gum composition.

The present invention also includes a method for preparing the improved chewing gum compositions, including both chewing gum and bubble gum formulations. The chewing gum compositions may be prepared using standard techniques and equipment known to those skilled in the art. The apparatus useful in accordance with the present invention comprises mixing and heating apparatus well known in the chewing gum manufacturing arts, and therefore the selection of the specific apparatus will be apparent to the skill artisan in the art.

In such a method, a chewing gum composition is made by admixing the present gum base with the other ingredients of the final desired chewing gum composition. Other ingredients will usually be incorporated into the composition as dictated by the nature of the desired composition as well known by those having ordinary skill in the art. The ultimate chewing gum compositions are readily prepared using methods generally known in the food technology and chewing gum arts.

For example, the present gum base is heated to a temperature sufficiently high to soften the base without adversely effecting the physical and chemical make up of the base. The optimal temperatures utilized may vary depending upon the composition of the gum base used, but such temperatures are readily determined by those skilled in the art without undue experimentation.

The gum base is conventionally melted at temperatures that range from about 60° C. to 120° C. for a period of time sufficient to render the base molten. For example, the gum base may be heated under these conditions for a period of about thirty minutes just prior to being admixed incrementally with the remaining ingredients of the gum composition such as the plasticizer, the softener, the bulking agent, the sweetener, and/or fillers, coloring agents and flavoring agents to plasticize the blend as well as to modulate the hardness, viscoelasticity and formability of the base. Mixing is continued until a uniform mixture of gum composition is obtained. Thereafter the gum composition mixture may be formed into desirable chewing gum shapes.

In accordance with the present invention, the gum base and chewing gum compositions incorporating the present gum base may be used as the outer shell of a center fill chewing gum enclosing a liquid center. The liquid center employed in this invention may be any liquid center well known in the art, including sugar and sugarless liquid centers. These liquid centers include, without limitation, substantially aqueous centers, aqueous centers containing additives such as thickeners, emulsifiers, humectants, binders, gums, and the like, and mixtures thereof to prevent migration of the liquid center, suspensions, and semi-liquid centers, wherein the viscosity of the liquid center can range from a gel-like consistency or pasty quality, to a relatively thixotropic, sticky liquid quality.

The liquid centers may contain those traditional ingredients well known in the chewing gum and confectionery arts such as flavoring agents, sweetening agents, and the like, and mixtures thereof. In addition to confectionery additives, the liquid centers may also contain pharmaceutical additives such as medicaments, breath fresheners, vitamins, fruit juices, and the like, and mixtures thereof. The confectionery and pharmaceutical agents may be used in many distinct physical forms well known in the art to provide an initial burst of sweetness and flavor and/or therapeutic activity or a prolonged sensation of sweetness and flavor and/or therapeutic activity. Without being limited thereto, such physical forms include free forms, such as spray dried, powdered, and beaded forms, and encapsulated forms, and mixtures thereof. Illustrative, but not limiting, examples of liquid centers suitable for use in the present invention include those centers disclosed in U.S. Pat. Nos. 3,894,154, 4,156,740, 4,157,402, 4,316,915, and 4,466,983, which disclosures are incorporated herein by reference.

Center fill chewing gum products of the present invention are typically formulated in individual serving pieces that may range in weight from about 3 grams up to about 7 grams. The weight of the individual serving pieces will vary in the desired range depending on several factors including, but not limited to, the target consumer group, the amount of stanol compounds to be administered per serving and the like.

The present invention extends to methods of making the stanol compound containing center fill chewing gum compositions. The improved compositions may be prepared using standard techniques and equipment known to those skilled in the art. The apparatus useful in accordance with the present invention comprises mixing and heating apparatus well known in the chewing gum manufacturing arts, and therefore the selection of the specific apparatus will be apparent to the artisan. Such methods and apparatus are disclosed, for example, in U.S. Pat. Nos. 3,806,290 and 3,857,963, which disclosures are incorporated herein by reference.

Typically, the gum base is fed into a gum extruder and extruded through an orifice as a hollow-centered rope of chewing gum. A liquid center formulation containing the stanol compounds is fed, under pressure, through an inner conduit to the hollow-center of the rope downstream of the orifice and the center-filled rope of chewing gum is passed into a sizing unit where rollers decrease the cross sectional dimension of the rope gum and form individual gum pieces.

The present invention is further illustrated by the following examples which are not intended to limit the effective scope of the claims. All parts and percentages in the examples and throughout the specification and claims are by weight of the final composition unless otherwise specified.

EXAMPLE 1

Preparation of Center Fill Chewing Gum

Containing Plant Stanol

Center fill chewing gum containing plant stanol of the present invention was prepared in the following manner.

TABLE 1

Gum Base Formulation

| Ingredients | Amount (% by weight) |
| --- | --- |
| 1) Gum base | 23.0 |
| 2) Lecithin | 0.6 |
| 3) Sorbitol | 49.705 |
| 4) Mannitol | 15.00 |
| 5) Glycerin | 9.5 |
| 6) High Intensity Sweetener | 0.775 |
| 7) Flavor | 1.42 |
| Total | 100.00 |

TABLE 2

Center Fill Formulation

| Ingredients | Amount (% by weight) |
| --- | --- |
| 1) Glycerin | 24.92 |
| 2) Sorbitol Solution | 24.546 |
| 3) Carboxymethyl cellulose | 37.38 |
| 4) Flavor | 0.135 |
| 5) High Intensity Sweetener-Acesulfame-K | 0.025 |
| 6) Plant stanol | 50.00 |
| Total | 100.00 |

The gum base formulation was prepared by blending the ingredients listed in Table 1 together in a gum extruder. The center fill formulation was prepared from the ingredients listed in Table 2. A solution blended from glycerin and sorbitol was prepared and heated to about 60° C. Carboxymethyl cellulose having a suitable molecular weight sufficient to provide a 2% aqueous solution with a viscosity of from about 2,500 to 5,000 cps, was slowly added to the glycerin and sorbitol solution and blended until completely dissolved. A high intensity sweetener such as acesulfame-K was added followed by the flavor. The plant stanol was then added to the mixture and continuously blended to prevent any separation. The finished gum product was formed by coextruding the gum base formulation through an orifice to produce a hollow-centered rope of chewing gum with the center fill formulation fed, under pressure, through an inner conduit to the hollow center of the rope. The resulting rope of center fill chewing gum was fed into a rotary sizing unit to form individual pieces of the final center fill chewing gum composition. The final center fill gum composition yielded pieces of chewing gum each weighing about 3.8 g and composed of 84% by weight gum base and 16% by weight center fill, each of which is based on the total weight of the chewing gum composition. The center fill portion was measured to contain about 304 mg of plant stanol per piece of finished chewing gum.

EXAMPLE 2

Preparation of Center Fill Chewing Gum Containing Plant Stanol

TABLE 3

Gum Base Formulation

| Ingredients | Amount (% by weight) |
| --- | --- |
| 1) Gum base | 21.5 |
| 2) Corn Syrup | 17.5 |
| 3) Lecithin | 0.3 |
| 4) Acetylated monoglycerides | 0.15 |
| 5) Glycerin | 1.0 |
| 6) Sugar | 58.8048 |
| 7) Flavor | 0.7452 |
| Total | 100.00 |

TABLE 4

Center Fill Formulation

| Ingredients | Amount (% by weight) |
| --- | --- |
| 1) Corn Syrup | 19.612 |
| 2) Sugar | 2.349 |
| 3) High Fructose Syrup | 19.612 |
| 4) Water | 2.531 |
| 5) Glycerin | 4.8991 |
| 6) Flavor | 0.9848 |
| 7) Plant stanol | 50.00 |
| Total | 100.00 |

The gum base formulation was prepared by blending the ingredients listed in Table 3 together in a gum extruder. The center fill formulation was prepared from the ingredients listed in Table 4. A solution blended from glycerin, sugar and water was prepared and heated to about 60° C. Corn syrup and high fructose syrup were thereafter added to the mixture followed by addition of the flavor. The plant stanol was then added to the mixture and continuously blended to prevent any separation. The finished gum product was formed by coextruding the gum base formulation through an orifice to produce a hollow-centered rope of chewing gum with the center fill formulation fed, under pressure, through an inner conduit to the hollow center of the rope. The resulting rope of center fill chewing gum was fed into a rotary sizing unit to form individual pieces of the final center fill gum composition. The final center fill gum composition yielded pieces of chewing gum each weighing about 3.8 g and composed of 84% by weight gum base and 16% by weight center fill, each of which is based on the total weight of the chewing gum composition. The center fill portion was measured to contain about 304 mg of plant stanol per piece of finished chewing gum.

EXAMPLE 3

Preparation of Chewing Gum Compositions Containing Plant Stanol

Gum cores containing a gum base composition containing butyl rubber, polyisobutylene, PVA (Polyvinylacetate), polyethylene, filler, and elastomer plasticizer were combined with a sufficient amount of plant stanol to provide from 1 to 2 g of plant stanol per piece. The gum cores were placed into a coating pan and broken into individual pieces. A sugarless solution containing 70% by weight of maltitol, as well as titanium dioxide, gum arabic and water was heated to between 70 and 80° C. The solution was sprayed on to the gum core pieces in layers and allowed to dry between sprays while the coating pan was continually rotating to ensure a smooth even coat of the gum cores.

The coating was built up to about 8% by weight of the final pellet weight. Ace-K was then added and then covered with another layer of the above-mentioned coating solution and then allowed to dry.

EXAMPLE 4

Preparation of Chewing Gum Compositions Containing Plant Stanol

A gum base as described in Example 3, was combined with a sufficient amount of plant stanol to provide from 1 to 2 g of plant stanol per piece of gum to produce an uncoated chewing gum composition containing an effective amount of plant stanol.

What is claimed is:

1. A chewing gum composition comprising an outer shell enclosing at least one cavity and a liquid center within the at least one cavity, and said liquid center comprising at least one stanol compound in an amount from about 1 to 90% by weight based on the total weight of the chewing gum composition, said amount being sufficient to provide a positive cholesterol effect when ingesting up to about seven individual serving portions per day.

2. The chewing gum composition of claim 1 wherein the at least one stanol compound is selected from the group consisting of a plant stanol, sterols and sterol fatty acid esters and derivatives thereof, and combinations thereof.

3. The chewing gum composition of claim 2 wherein the at least one stanol compound is selected from the group consisting of beta-sitosterol, campesterol, stigmasterol, brassicasterol, cycloartenol, cyclobranol and combinations thereof.

4. The chewing gum composition of claim 2 wherein the at least one stanol compound is selected from the group consisting of a plant stanol.

5. The chewing gum composition of claim 1 wherein the amount of at least one stanol compound is present from about 20% to 70% by weight based on the total weight of the chewing gum composition.

6. The chewing gum composition of claim 1 wherein no more than four serving portions of the chewing gum composition per day are employed to obtain the positive cholesterol effect.

7. The chewing gum composition of claim 1 wherein the positive cholesterol effect is a cholesterol reducing effect.

8. The chewing gum composition of claim 1 wherein the effective amount of the at least one stanol compound is from about 1.0 to 2.0 g per day.

9. The chewing gum composition of claim 1 wherein the at least one stanol compound is present in an amount of from about 100 mg to 500 mg.

10. The chewing gum composition of claim 9 wherein the at least one stanol compound is present in an amount from about 300 mg to 480 mg.

11. The chewing gum composition of claim 1 wherein the outer shell comprises a gum base.

12. A method of forming a chewing gum composition having a positive cholesterol effect comprising forming a liquid center formulation containing an effective amount of at least one stanol compound and combining the liquid center formulation with an outer shell formulation to form a center fill chewing gum composition containing from about 1 to 90% by weight of at least one stanol compound based on the total weight of the chewing gum composition, said amount being sufficient to provide a positive cholesterol effect when ingesting up to seven individual serving portions per day.

13. A method of reducing or maintaining cholesterol levels in a warm-blooded animal, comprising administering to the warm-blooded animal with an effective amount of the chewing gum composition of claim 1.

14. The method of claim 12 wherein the amount of the at least one plant stanol compound is from about 20 to 70% by weight based on the total weight of the chewing gum composition.

* * * * *